United States Patent
Robinson et al.

(10) Patent No.: US 11,135,299 B2
(45) Date of Patent: Oct. 5, 2021

(54) CHEMOSELECTIVE MODIFICATION OF A CARRIER PROTEIN WITH A STRAINED ALKYNE-LABELED CARGO AGENT

(71) Applicant: The Regents of the University of California, Oakland, CA (US)

(72) Inventors: Peter V. Robinson, Berkeley, CA (US); Cheng-Ting Tsai, Berkeley, CA (US); Carolyn R. Bertozzi, Berkeley, CA (US)

(73) Assignee: the regents of the university of california, Oakland, CA (US)

( * ) Notice: Subject to any disclaimer, the term of this patent is extended or adjusted under 35 U.S.C. 154(b) by 0 days.

(21) Appl. No.: 15/576,226

(22) PCT Filed: Jun. 16, 2016

(86) PCT No.: PCT/US2016/037910
§ 371 (c)(1),
(2) Date: Nov. 21, 2017

(87) PCT Pub. No.: WO2016/205545
PCT Pub. Date: Dec. 22, 2016

(65) Prior Publication Data
US 2018/0147288 A1    May 31, 2018

Related U.S. Application Data
(60) Provisional application No. 62/180,879, filed on Jun. 17, 2015.

(51) Int. Cl.
| | | |
|---|---|---|
| *A61P 29/00* | (2006.01) |
| *A61K 47/54* | (2017.01) |
| *A61K 47/64* | (2017.01) |
| *A61P 31/00* | (2006.01) |
| *A61P 35/00* | (2006.01) |
| *C12N 15/115* | (2010.01) |

(52) U.S. Cl.
CPC .......... *A61K 47/545* (2017.08); *A61K 47/555* (2017.08); *A61K 47/643* (2017.08); *A61P 29/00* (2018.01); *A61P 31/00* (2018.01); *A61P 35/00* (2018.01); *C12N 15/115* (2013.01)

(58) Field of Classification Search
None
See application file for complete search history.

(56) References Cited

U.S. PATENT DOCUMENTS

| | | |
|---|---|---|
| 8,461,298 B2 | 6/2013 | Bertozzi et al. |
| 2013/0231473 A1* | 9/2013 | Brown .................. C07H 21/04 536/25.32 |

OTHER PUBLICATIONS

Ning, et al.; "Visualizing Metabolically Labeled Glycoconjugates of Living Cells by Copper-Free and Fast Huisgen Cycloadditions," Angew CHem Int Ed (2008), 47, 2253-2255 (Year: 2008).*
Debets, M.F. et al., "Aza-dibenzocyclooctynes for fast and efficient enzyme PEGylation via copper-free (3+2) cycloaddition," Chem. Commun, 2010, 46, 97-99 (Year: 2010).*
Agarwal, et al.; "Site-Specific Antibody-Drug Conjugates: The Nexus of Bioorthogonal Chemistry, Protein Engineering, and Drug Development"; Bioconjugate Chem.; vol. 26, pp. 176-192 (Dec. 12, 2014).
Conte, et al.; "Multi-molecule reaction of serum albumin can occur through thiol-yne coupling"; Chem. Commun.; vol. 47, pp. 11086-11088 (2011).
Debets, et al.; "Bioorthogonal labelling of biomolecules: new functional handles and ligation methods"; Org. Biomol. Chem.; vol. 11, pp. 6439-6455 (2013).
Ning, et al.; "Protein Modification by Strain-Promoted Alkyne-Nitrone Cycloaddition"; Angew Chem Int Ed Engl.; vol. 49, No. 17, pp. 3065-3068 (Apr. 12, 2010).
Simon, et al.; "Orthogonal Assembly of a Designed Ankyrin Repeat Protein-Cytotoxin Conjugate with a Clickable Serum Albumin Module for Half-Life Extension"; Bioconjugate Chemistry; vol. 24, pp. 1955-1966 (2013).
Spicer, et al.; "Selective chemical protein modification"; Nat. Commun.; vol. 5, No. 4740, pp. 1-14 (Sep. 5, 2014).
Umezawa; "Inhibition of tumor growth by NF-κB inhibitors"; Cancer Sci; vol. 87, No. 10, pp. 990-995 (Oct. 2006).

* cited by examiner

*Primary Examiner* — Thomas S Heard
(74) *Attorney, Agent, or Firm* — Bozicevic, Field & Francis LLP; Paula A. Borden

(57) ABSTRACT

Pharmaceutical compositions are provided for extending the serum half-life of a therapeutic agent. The composition may include a strained alkyne-labeled therapeutic agent. Also provided is a strained alkyne-carrier protein adduct including a vinyl thioether-linkage to a cysteine residue of the carrier protein. Methods of chemoselectively modifying a carrier protein are provided, that include conjugating a cysteine residue of a carrier protein with a cyclooctyne-labeled cargo agent to produce a vinyl thioether-linked conjugate. Also provided is a method of increasing the in vivo half-life of a bioactive agent including administering a strained alkyne-labeled bioactive agent to a subject.

6 Claims, 6 Drawing Sheets

US 11,135,299 B2

1

CHEMOSELECTIVE MODIFICATION OF A CARRIER PROTEIN WITH A STRAINED ALKYNE-LABELED CARGO AGENT

CROSS-REFERENCE

This application claims the benefit of U.S. Provisional Patent Application No. 62/180,879, filed Jun. 17, 2015, which application is incorporated herein by reference in its entirety.

STATEMENT REGARDING FEDERALLY SPONSORED RESEARCH

This invention was made with government support under Grant No. GM059907 awarded by the National Institutes of Health. The government has certain rights in the invention.

INTRODUCTION

Serum albumin is an abundant and long-lived blood protein with important biotechnological applications. Its primary functions are to sustain oncotic pressure within tissues and solubilize hydrophobic molecules. Due to its lengthy 19-day half life, conjugation to albumin is recognized as a strategy for extending the serum-half life of short-lived therapeutics, thereby increasing the therapeutic window. Other applications exploit the natural pooling of albumin in the lymph nodes for monitoring proper lymph function or for improved display of vaccine antigens and adjuvants to dendritic cells.

There is a need in the art for methods of conjugating therapeutic agents to protein carriers such as serum albumin.

SUMMARY

Pharmaceutical compositions are provided for extending the serum half-life of a therapeutic agent. The composition may include a strained alkyne-labeled therapeutic agent. Also provided is a strained alkyne-carrier protein adduct including a vinyl thioether-linkage to a carrier protein. Methods of chemoselectively modifying a carrier protein are provided, that include conjugating a cysteine residue of a carrier protein with a cyclooctyne-labeled cargo agent to produce a vinyl thioether-linked conjugate. Also provided is a method of increasing the in vivo half-life of a bioactive agent including administering a strained alkyne-labeled bioactive agent to a subject.

2

Figure 5:
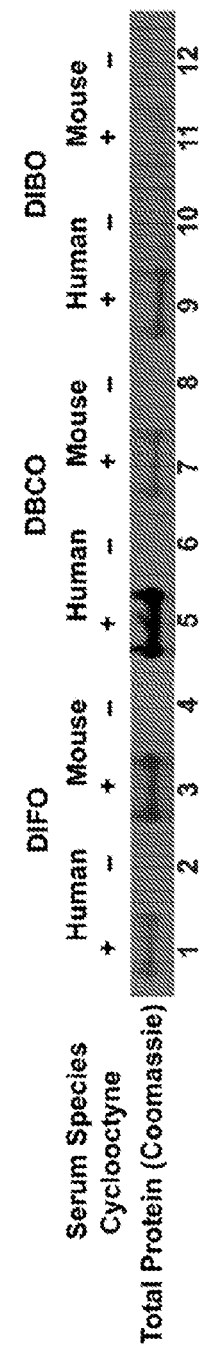

FIG. 5 shows polyacrylamide gel images that illustrate streptavidin enrichment of biotinylated albumin by labelling with biotin-cyclooctyne conjugate in human or mouse serum.

Figure 6:
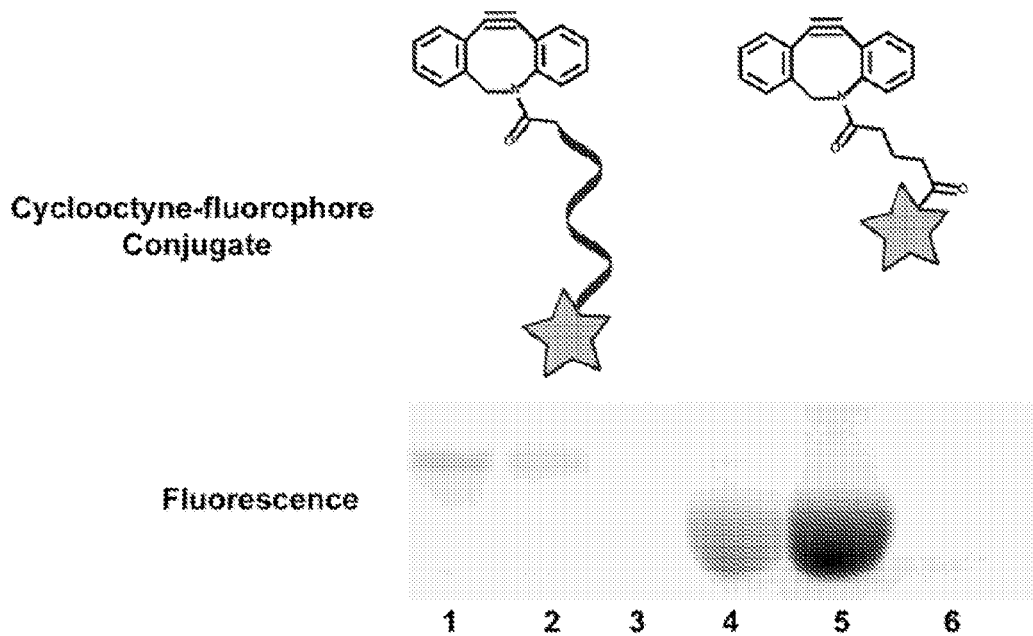

FIG. 6 illustrates aptamer-cyclooctyne conjugates label albumin in whole serum. Cyclooctyne-fluorophore conjugates (fluorophore-cyclooctyne-aptamer conjugate in Lanes 1-3, cyclooctyne-fluorophore conjugate in Lanes 4-6) were incubated with whole human serum (Lanes 1 and 4), purified human albumin (Lanes 2 and 5), or PBS (Lanes 3 and 6) for 2 h at 37° C.

DEFINITIONS

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. The terms also include polypeptides that have co-translational (e.g., signal peptide cleavage) and post-translational modifications of the polypeptide, such as, for example, disulfide-bond formation, glycosylation, acetylation, phosphorylation, proteolytic cleavage (e.g., cleavage by furins or metalloproteases), and the like. Furthermore, as used herein, a "polypeptide" refers to a protein that includes modifications, such as deletions, additions, and substitutions (generally conservative in nature as would be known to a person in the art) to the native sequence, as long as the protein maintains the desired activity. These modifications can be deliberate, as through site-directed mutagenesis, or can be accidental, such as through mutations of hosts that produce the proteins, or errors due to polymerase chain reaction (PCR) amplification or other recombinant DNA methods.

The terms "polynucleotide," "oligonucleotide," "nucleic acid" and "nucleic acid molecule" are used interchangeably herein to include a polymeric form of nucleotides, either ribonucleotides or deoxyribonucleotides. This term refers only to the primary structure of the molecule. Thus, the terms include triple-, double- and single-stranded DNA, as well as triple-, double- and single-stranded RNA. The terms also include such molecules with modifications, such as by methylation and/or by capping, and unmodified forms of a polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing non-nucleotidic backbones, polymers, and other synthetic sequence-specific nucleic acid polymers providing that the polymers contain nucleobases in a configuration which allows for base pairing and base stacking, such as is found in DNA and RNA.

By "specifically binds" or "selectively bind" is meant that the molecule binds preferentially to the target of interest or binds with greater affinity to the target than to other molecules. For example, a DNA molecule will bind to a substantially complementary sequence and not to unrelated sequences. Specific binding may refer to non-covalent or covalent preferential binding to a molecule relative to other molecules or moieties in a solution or reaction mixture (e.g., an antibody specifically binds to a particular polypeptide or epitope relative to other available polypeptides). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides or polypeptides. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, blood fractions such as plasma and serum, and the like. The term "biological sample" also includes solid tissue samples, tissue culture samples, and cellular samples.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

The term "subject" as used herein refers to an animal, including mammals such as humans, livestock, pets, laboratory animals, bioproduction animals (e.g., animals used to generate a bioproduct, e.g., an antibody), and the like. In some instances, a sample is derived from a mammalian subject, including e.g., mammalian tissue, mammalian cells, mammalian bodily fluid, mammalian excreted bodily fluids, mammalian semi-solid secretions, and the like. Mammals of interest include but are not limited to e.g., humans, ungulates (e.g., any species or subspecies of porcine (pig), bovine (cattle), ovine (sheep) and caprine (goats), equine (horses) or, generally, hooved domestic or farm animals, etc.), rodents (e.g., mice, rats, gerbils, hamsters, guinea pigs, and the like), rabbits, cats, dogs, primates, and the like.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The term "cytotoxic agent" as used herein refers to a substance that inhibits or prevents the function of cells and/or causes destruction of cells. The term is intended to include radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$P, and radioactive isotopes of Lu), chemotherapeutic agents, and toxins such as small molecule toxins or enzymatically active toxins of bacterial, fungal, plant or animal origin, including synthetic analogs and derivatives thereof.

The term "label" means any moiety which can be covalently attached to a carrier protein, e.g., via a strained alkyne conjugate, and that functions to: (i) provide a detectable signal; (ii) interact with a second label to modify the detectable signal provided by the first or second label, e.g. FRET (fluorescence resonance energy transfer); (iii) stabilize interactions or increase affinity of binding, e.g., with a ligand; (iv) affect mobility, e.g. electrophoretic mobility, or cell-permeability, by charge, hydrophobicity, shape, or other physical parameters, or (v) provide a capture moiety, to modulate ligand affinity, antibody/antigen binding, or ionic complexation.

The phrase "pharmaceutically acceptable salt," as used herein, refers to pharmaceutically acceptable organic or inorganic salts of the subject compositions. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a strained cycloalkyne" includes a plurality of such strained cycloalkynes and reference to "the strained cycloalkyne" includes reference to one or more strained cycloalkynes and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

Figure 1:
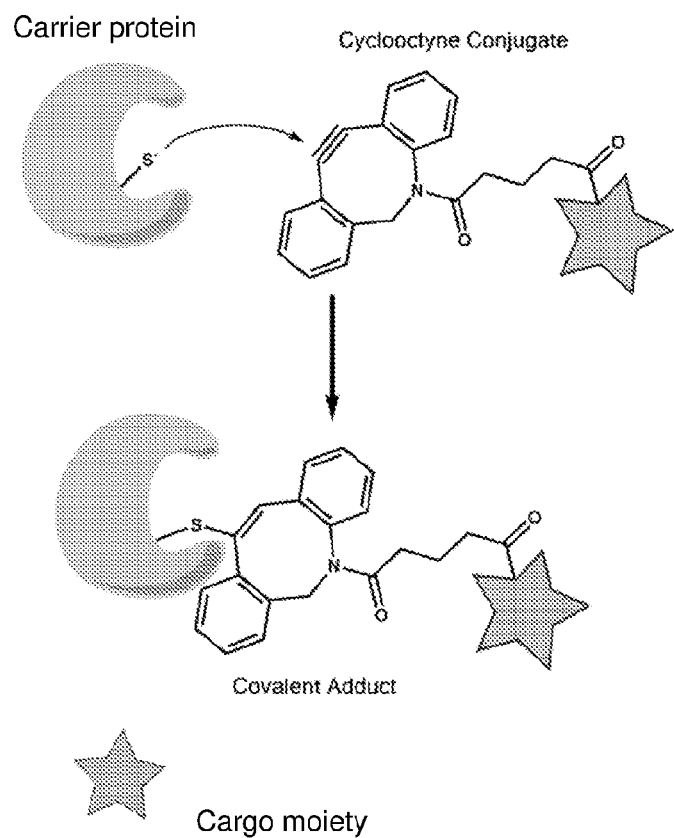
FIG. 1 depicts a cyclooctyne conjugate of interest binding to a carrier protein (e.g., serum albumin) via a cysteine residue to produce a stable vinyl thioether linkage (e.g., covalent adduct). The cargo moiety (e.g., a reporter such as a fluorophore or a biotin, or a bioactive molecule such as a small molecule, a peptide or a nucleic acid) attached to the cyclooctyne may have a longer serum half-life due to conjugation to the carrier albumin.

As summarized above, methods of chemoselectively modifying a carrier protein and compositions for achieving the same are provided. Aspects of the present disclosure include the utilization of a strain-induced reactivity of alkynes towards thiols to achieve in vivo chemoselective conjugation to carrier proteins of interest. Chemoselective modification is achieved via a thiol-yne reaction involving the reaction of a thiol with a strained alkyne to form a stable vinyl thioether. Alkynes such as cyclooctynes are components of copper-free click chemistry conjugation reactions due to their pericylic reactivity with azides and other pi systems. FIG. 1 depicts an exemplary conjugation reaction of the subject method between a carrier protein and a strained alkyne of interest (e.g., a cyclooctyne). In some embodiments, the method includes conjugating a cysteine residue of a carrier protein with a strained alkyne-labeled cargo agent to produce a vinyl thioether-linked conjugate. In general terms, the cysteine residue (or free thiol) of a carrier protein may be conjugated with a strained alkyne moiety connected to a cargo agent of interest to produce an adduct of the carrier protein that is connected via a vinyl thioether linkage.

The cysteine-strained alkyne conjugation reaction may occur under a variety of convenient conditions. In some cases, the conjugation reaction is performed in vivo. As such, the method may include administering to a subject a pharmaceutical composition including a strained alkyne-labeled cargo agent (e.g., as described herein). In certain cases, the conjugation reaction is performed in vitro. In some cases, the method includes conjugating a cysteine residue of a carrier protein with a cyclooctyne-labeled cargo agent to produce a vinyl thioether-linked conjugate. As used herein, the terms conjugate and adduct are used interchangeably to refer to the product of a conjugation reaction. The conjugation reaction may be performed in aqueous conditions or in an organic solvent. The conjugation reaction may be performed under a variety of pH conditions where the thiol group is nucleophilic. The conjugation reaction may be performed under physiological conditions, e.g., physiological temperature, pH, etc. Cysteine thiols are reactive at neutral pH, unlike most amines which are protonated and less nucleophilic near pH 7.

Strained Alkyne-Labeled Cargo Agent

In some embodiments, the strained alkyne moiety which chemoselectively modifies the carrier protein is a strained alkyne-labeled cargo agent that includes a cargo agent of interest that is labelled with one or more strained alkynes. In some cases, the strained alkyne-labeled cargo agent is a multimer that includes two or more cargo agents connected to a strained alkyne, e.g., via a branched linker. As used herein, the term "strained alkyne-labeled" refers to a moiety to which a strained alkyne group or molecule has been covalently attached, via an optional linker. Covalent attachment may be performed using a variety of methods and functional group chemistries. Exemplary covalent linkages may be utilized in the labelling of a cargo agent of interest, include but are not limited to, amide or ester bond linkages, e.g., via reaction of an amino or hydroxyl group with a carboxylic acid or derivative thereof (e.g., an active ester); carbamate linkages; ether linkages, e.g., via reaction of a hydroxyl group and an electrophilic carbon (e.g., a bromoalkyl); amino linkage, e.g., via reductive amination, etc.

In some embodiments, the strained alkyne-labeled cargo agent may be described by Formula (I):

$$Z\text{-}L\text{-}Y \tag{I}$$

wherein: Z is a strained alkyne; L is an optional linker; and Y is a cargo agent.

In some cases, the strained alkyne-labeled cargo agent is a cyclooctyne-labeled cargo agent.

As used herein, the term "linker" or "linkage" refers to a linking moiety that connects two groups and has a backbone of 100 atoms or less in length. A linker or linkage may be a covalent bond that connects two groups or a chain of between 1 and 100 atoms in length, for example of 1, 2, 3, 4, 5, 6, 8, 10, 12, 14, 16, 18 or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, poly(ethylene glycol); ethers, thioethers, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

Strained Alkynes

As used herein, the term "strained alkyne" refers to an alkyne containing group or molecule where the alkyne has increased reactivity due to an inherent steric strain (e.g., a ring strain) on the linear alkyne group. An alkyne of interest may be strained in a variety of ways, such as the introduction of a ring structure, or the introduction of steric repulsion into the alkyne containing group to place mechanical stress on the carbon-carbon triple bond which can increase its reactivity. Strained alkynes of interest include those that find use in strain-promoted azide alkyne cycloaddition reactions (SPAAC), including azide bioconjugation reactions. In some cases, the "strained alkyne" is a cyclic alkyne, such as a cycloheptyne, a cyclooctyne, a cyclononyne, or a heterocyclic analog thereof.

A variety of strained alkynes may be adapted for incorporation into a strained alkyne-labeled cargo agent as described herein, e.g., in Formula (I). Any of the strained alkynes described herein may be adapted to include an optional linker for attachment to a cargo agent, e.g., via covalent attachment of a linker or cargo agent to a hydroxyl group or a carboxylic acid group, or derivative thereof, of the strained alkynes described herein.

In certain embodiments, the strained alkyne is described by the formula:

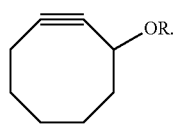

OCT 1: R = CH$_2$PhCO$_2$H
OCT 2: R = CH$_2$CO$_2$H

In certain embodiments, the strained alkyne is described by the formula:

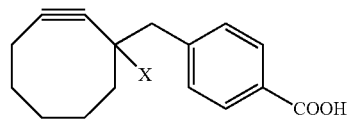

OCT 3: R = H
MOFO: R = F where X in some cases may be H or F.

In certain embodiments, the strained alkyne is described by the formula:

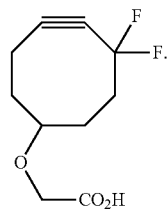

In certain embodiments, the strained alkyne is described by the formula:

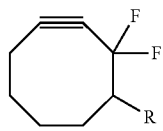

DIFO 2: R = CH$_2$PhCO$_2$H
DIFO 3: R = CH$_2$CO$_2$H .

In certain embodiments, the strained alkyne is described by the formula:

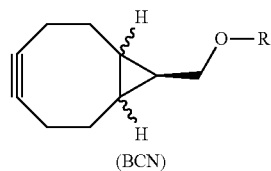

(BCN)

where R is H or an optional linker.

In certain embodiments, the strained alkyne is described by the formula:

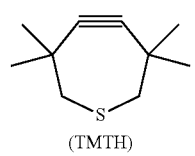

(TMTH)

where an optional linker or cargo agent may be attached at any convenient location of the TMTH strained alkyne, such as at a ring position alpha to the S atom.

In certain embodiments, the strained alkyne is described by the formula:

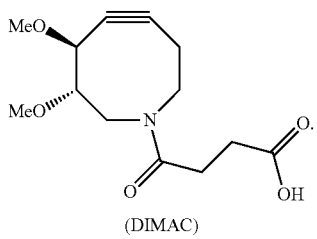 [SMILES: CO[C@H]1C#CCCN(C(=O)CCC(=O)O)C[C@@H]1OC]

(DIMAC)

In certain embodiments, the strained alkyne is described by the formula:

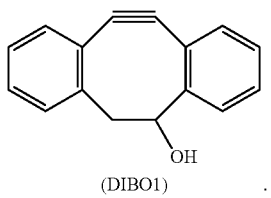

(DIBO1)

In certain embodiments, the strained alkyne is described by the formula:

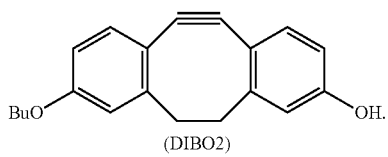

(DIBO2)

In certain embodiments, the strained alkyne is described by the formula:

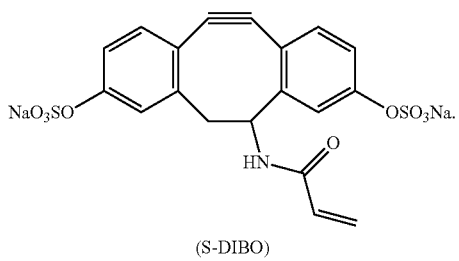

(S-DIBO)

In certain embodiments, the strained alkyne is described by the formula:

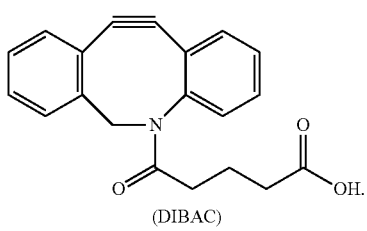

(DIBAC)

In certain embodiments, the strained alkyne is described by the formula:

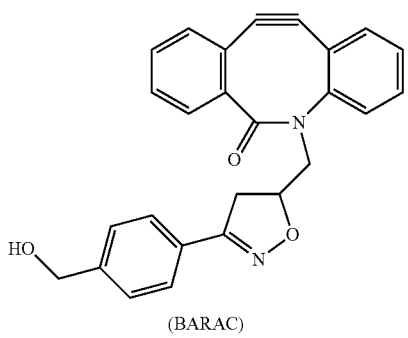

(BARAC)

In certain embodiments, the strained alkyne is described by the formula:

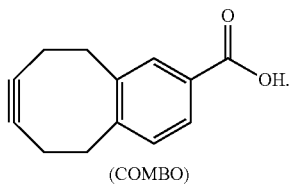

(COMBO)

Cyclooctynes of interest include, but are not limited to, dibenzoazocyclooctyne (DBCO/DIBAC), a dibenzocyclooctyne (DIBO) (e.g., DIBO1, DIBO2 or S-DIBO), a difluorocyclooctyne (DIFO) (e.g., DIFO1, 2 or 3), OCT1, OCT2, OCT3, MOFO, BCN, TMTH, DIMAC, BARAC, COMBO, and fluorogenic cyclooctynes such as CoumBARAC or F1-DIBO. In certain embodiments, the cyclooctyne is selected from: dibenzoazocyclooctyne, a dibenzocyclooctyne, a difluorocyclooctyne, OCT1, OCT2, OCT3, MOFO, BCN, TMTH, DIMAC, BARAC and COMBO.

In some embodiments, the cyclooctyne is selected from:

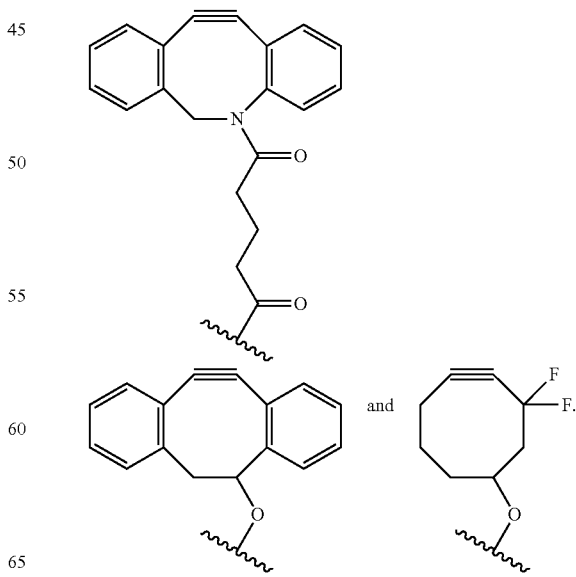

The strained alkyne may be covalently attached to a cargo agent of interest directly or indirectly via an optional linker (e.g., as described herein). Exemplary linking groups and linkages and methods of using the same are described in e.g., Hermanson, "Bioconjugate Techniques" 2nd Edition, Academic Press, 2008. The linker may be cleavable or non-cleavable. In some cases, the linker includes a group selected from the group consisting of $(C_1\text{-}C_{12})$alkyl, a substituted $(C_1\text{-}C_{12})$alkyl, $(EDA)_w$ where EDA is an ethylenediamino group, $(PEG)_n$, where PEG is a polyethyleneglycol group, $(AA)_p$, where AA is an amino acid residue, para-amino-benzyloxycarbonyl (PABC), a meta-amino-benzyloxycarbonyl (MABC), a para-amino-benzyloxy (PABO), a meta-amino-benzyloxy (MABO), para-aminobenzyl, an acetal group, a disulfide, a protease-cleavable moiety, a glucuronidase cleavable moiety, a beta-lactamase cleavable moiety, and an ester.

For instance, in certain embodiments of Formula (I), L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments of Formula (I), L includes an alkyl or substituted alkyl group. In certain embodiments of Formula (I), L includes an alkenyl or substituted alkenyl group. In certain embodiments of Formula (I), L includes an alkynyl or substituted alkynyl group. In certain embodiments of Formula (I), L includes an alkoxy or substituted alkoxy group. In certain embodiments of Formula (I), L includes an amino or substituted amino group. In certain embodiments of Formula (I), L includes a carboxyl or carboxyl ester group. In certain embodiments of Formula (I), L includes an acyl amino group. In certain embodiments of Formula (I), L includes an alkylamide or substituted alkylamide group. In certain embodiments of Formula (I), L includes an aryl or substituted aryl group. In certain embodiments of Formula (I), L includes a heteroaryl or substituted heteroaryl group. In certain embodiments of Formula (I), L includes a cycloalkyl or substituted cycloalkyl group. In certain embodiments of Formula (I), L includes a heterocyclyl or substituted heterocyclyl group.

In certain embodiments of Formula (I), L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol.

Cargo Agents

As used herein, the term "cargo agent" refers to any convenient moiety that may be covalently attached to a strained alkyne group via an optional linker. Any convenient cargo agents may be utilized in the subject strained alkyne-labelled cargo agents for conjugation to a carrier protein of interest. The cargo agent may be an organic small molecule, a peptide, a protein, a nucleic acid, a polymer or a lipid. The cargo agent may be a bioactive agent (e.g., a therapeutic agent or an immunomodulatory agent). The cargo agent may be a detectable agent (e.g., detectable label or a chelating agent). The cargo agent can be an anti-inflammatory agent, an immunomodulatory agent, an antiviral agent, an anti-inflammatory agent, a cancer chemotherapeutic agent, and the like.

Cargo agents of interest include, but are not limited to, an immunomodulatory agent, a therapeutic agent such as small molecule drug, a cytotoxic agent, an affinity ligand, a diagnostic agent, a detectable label, a chelating agent (e.g., for an imaging or radiotherapeutic metal), a peptidyl tag, a clearance-modifying agent (e.g., a polyethylene glycol, a nucleic acid, or a peptide that binds to a third component).

Any convenient immunomodulatory agent may find use in the subject strained alkyne-labelled cargo agents. As used herein, the term "immunomodulatory agent" means an agent that modulates an immune response. "Modulate", as used herein, refers to inducing, enhancing, stimulating, or directing an immune response. In some cases, such agents include an antigen or an adjuvant. In some cases, such agents include immunostimulatory agents that stimulate (or boost) an immune response to an antigen but is not an antigen or derived from an antigen. Immunomodulatory agents of interest include, but are not limited to, cytokines, chemokines, growth factors, and the like. Immunomodulatory agents of interest include, but are not limited to, resiquimod, interleukins, interferons, GM-CSF, tumor necrosis factor-alpha (TNFalpha), TNFbeta, cyclosporine A, FK506, azathioprine, steroids, and fragments thereof and analogs thereof, such as those agents described in U.S. Pat. No. 5,639,852.

In some cases, the cargo agent is an anti-inflammatory agent. Suitable anti-inflammatory agents include, but are not limited to, TNF-α inhibitors such as anti-TNF-α monoclonal antibodies (such as REMICADE, CDP-870) and D2E7 (HUMIRA) and TNF receptor immunoglobulin fusion molecules (such as ENBREL), IL-1 inhibitors, receptor antagonists or soluble IL-1Rα (e.g. KINERET or ICE inhibitors), nonsterodial anti-inflammatory agents (NSAIDS), piroxicam, diclofenac, naproxen, flurbiprofen, fenoprofen, ketoprofen, ibuprofen, fenamates, mefenamic acid, indomethacin, sulindac, apazone, pyrazolones, phenylbutazone, aspirin, cyclooxygenase-2 (COX-2) inhibitors (such as CELEBREX (celecoxib), PREXIGE (lumiracoxib)), metalloprotease inhibitors (e.g., MMP-13 selective inhibitors), p2x7 inhibitors, NEUROTIN, pregabalin, methotrexate, leflunomide, hydroxyxchloroquine, d-penicillamine, auranofin, and the like.

In some cases, the cargo agent is a non-steroidal anti-inflammatory agent (NSAID), where suitable NSAIDs include, e.g., piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, lumiracoxib and etoricoxib, corticosteroids, and hyaluronic acids such as hyalgan and synvisc.

In some cases, the cargo agent is an anti-viral agent. Suitable anti-viral agents include, e.g., Viracept, AZT, acyclovir and famciclovir.

In some cases, the cargo agent is an anti-depressant (e.g., sertraline). In some cases, the cargo agent is an agent for treating Parkinson's disease, where suitable such agents include, e.g., deprenyl, L-dopa, Requip, and Mirapex. In some cases, the cargo agent is an agent for treating Alzheimer's disease, where suitable such agents include, e.g., donepezil, tacrine, α2δinhibitors, NEUROTIN, pregabalin, COX-2 inhibitors, propentofylline, and metryfonate.

In some cases, the cargo agent is a cardiovascular agent including, for example, an anti-arrhythmic agent, an antihypertensive agent, a calcium channel blocker, a cardioplegic solution, a cardiotonic agent, a fibrinolytic agent, a sclerosing solution, a vasoconstrictor agent, a vasodilator agent, a nitric oxide donor, a potassium channel blocker, a sodium channel blocker, statins, or a naturiuretic agent.

In some cases, the cargo agent is an anti-arrhythmia agent. Suitable anti-arrhythmia agents include, e.g., lidocaine, moricizine, mexiletine, tocainide, procainamide, encainide, flecanide, tocainide, phenyloin, propafenone, quinidine, disopyramide, and flecainide. Suitable anti-arrhythmia agents include, e.g., propranolol and esmolol. Suitable anti-arrhythmia agents include, e.g., amiodarone, artilide, bretylium, clofilium, isobutilide, sotalol, azimilide, dofetilide, dronedarone, ersentilide, ibutilide, tedisamil, and trecetilide. Suitable anti-arrhythmia agents include, e.g., verapamil, diltaizem, *digitalis*, and adenosine.

Suitable cardiovascular agents include vasodilators, for example, hydralazine; angiotensin converting enzyme inhibitors, for example, captopril; anti-anginal agents, for example, isosorbide nitrate, glyceryl trinitrate and pentaerythritol tetranitrate; anti-arrhythmic agents, for example, quinidine, procainaltide and lignocaine; cardioglycosides, for example, digoxin and digitoxin; calcium antagonists, for example, verapamil and nifedipine; diuretics, such as thiazides and related compounds, for example, bendrofluazide, chlorothiazide, chlorothalidone, hydrochlorothiazide and other diuretics, for example, fursemide and triamterene, and sedatives, for example, nitrazepam, flurazepam and diazepam.

In some cases, the cargo agent is an anti-hypertensive agent. Suitable antihypertensive agents include angiotensin converting enzyme inhibitors (such as captopril, alacepril, lisinopril, imidapril, quinapril, temocapril, delapril, benazepril, cilazapril, trandolapril, enalapril, ceronapril, fosinopril, imadapril, mobertpril, perindopril, ramipril, spirapril, and randolapril), angiotensin II antagonists (such as losartan, candesartan, valsartan, eprosartan, and irbesartan), calcium channel blocking drugs (such as aranidipine, efonidipine, nicardipine, bamidipine, benidipine, manidipine, cilnidipine, nisoldipine, nitrendipine, nifedipine, nilvadipine, felodipine, amlodipine, diltiazem, bepridil, clentiazem, phendilin, galopamil, mibefradil, prenylamine, semotiadil, terodiline, verapamil, cilnidipine, elgodipine, isradipine, lacidipine, lercanidipine, nimodipine, cinnarizine, flunarizine, lidoflazine, lomerizine, bencyclane, etafenone, and perhexyline), β-adrenaline receptor blocking drugs (propranolol, pindolol, indenolol, carteolol, bunitrolol, atenolol, acebutolol, metoprolol, timolol, nipradilol, penbutolol, nadolol, tilisolol, carvedilol, bisoprolol, betaxolol, celiprolol, bopindolol, bevantolol, labetalol, alprenolol, amosulalol, arotinolol, befunolol, bucumolol, bufetolol, buferalol, buprandolol, butylidine, butofilolol, carazolol, cetamolol, cloranolol, dilevalol, epanolol, levobunolol, mepindolol, metipranolol, moprolol, nadoxolol, nevibolol, oxprenolol, practol, pronetalol, sotalol, sufinalol, talindolol, tertalol, toliprolol, xybenolol, and esmolol), α-receptor blocking drugs (such as amosulalol, prazosin, terazosin, doxazosin, bunazosin, urapidil, phentolamine, arotinolol, dapiprazole, fenspiride, indoramin, labetalol, naftopidil, nicergoline, tamsulosin, tolazoline, trimazosin, and yohimbine), sympathetic nerve inhibitors (such as clonidine, guanfacine, guanabenz, methyldopa, and reserpine), hydralazine, todralazine, budralazine, and cadralazine.

Any convenient therapeutic agent may find use in the subject strained alkyne-labelled cargo agents. Therapeutic agents of interest include, but are not limited to, a drug for treating cancer (e.g., colorectal, breast, prostate, lung, head-and-neck, pancreatic, stomach, or ovarian cancer, or lymphomas, leukemias, astrocytomas, or hepatocellular carcinomas); cardiovascular disease; obesity; viral, bacterial, fungal or other infections; inflammation; neurological disorders; degenerative neurological disorders; psychiatric diseases or conditions; depression; hormonal disorders; glucose metabolism disorders or diabetes. In some cases, the cargo agent is an agent that finds use in contraception. In some embodiments, the therapeutic agent is selected from the group consisting of small molecules (e.g., nucleotide, steroid or other organic compound), polynucleotides, a lipid and a polypeptide (e.g., antibody or antibody fragment, growth hormone, or GLP1).

In some cases, the therapeutic agent is a small molecule drug. "Small molecule drug" as used herein refers to a compound, e.g., an organic compound, naturally occurring or non-naturally occurring, which exhibits a pharmaceutical activity of interest and which is generally of a molecular weight of 800 Da or less, or 2000 Da or less, but can encompass molecules of up to 5 kDa and can be as large as 10 kDa. One exemplary class of therapeutic agent is cytotoxic agents. In some cases, the cytotoxic agents are chemotherapeutic agents. Exemplary chemotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, duocarmycin, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol™), pilocarpine, prochloroperazine, rituximab, saproin, tamoxifen, taxol, topotecan hydrochloride, trastuzumab, vinblastine, vincristine and vinorelbine tartrate. In some cases, the cargo agent is an anthracycline chemotherapeutic compound, such as doxorubicin (DOX).

In certain embodiments, the therapeutic agent is selected from growth hormone, GLP1, GLP2, folate, exendin4 and doxorubicin.

Therapeutic agent moieties of interest also include dolastatins and their peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division and have anticancer (U.S. Pat. No. 5,663,149) and antifungal activity. Various forms of a dolastatin or auristatin drug moiety may be covalently attached to a strained alkyne through the N (amino) terminus or the C (carboxyl) terminus of the peptidic drug moiety. Exemplary auristatin embodiments include the N-terminus linked monomethylauristatin drug moieties DE, DF, MMAE and MMAF.

In some cases, the cargo agent is a therapeutic antibody. Suitable therapeutic antibodies include, but are not limited to, adalimumab, bevacizumab, infliximab, abciximab, alemtuzumab, bapineuzumab, basiliximab, belimumab, briakinumab, brodalumab, canakinumab, certolizumab pegol, cetuximab, conatumumab, denosumab, eculizumab, etrolizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumornab, pertuzumab, ranibizumab, rituximab, rovelizumab, tocilizumab, tositumomab, trastuzumab, ustekinumab, vedolizomab, zalutumumab, and zanolimumab.

In some cases, the cargo agent is a diagnostic agent. A diagnostic agent is any convenient molecule that finds use in the diagnosis of disease. In some case, the diagnostic agent is an agent for diagnostic imaging techniques, fluorescence-based techniques, angiography, fluoroangiography, ultrasonography, magnetic resonance-based diagnostic procedures, magnetic resonance imaging, X-ray imaging, nuclear medicine, single photon emission computed tomography (SPECT) or positron emission tomography (PET), a fluorophore for opthalmological angiography or a contrast agent for X-ray or magnetic resonance imaging. In some cases, the diagnostic agent is a radiopharmaceutical imaging molecule that finds use in in vivo imaging. In some cases, the diagnostic agent is a detectable label.

Any convenient affinity ligand may find use in the subject strained alkyne-labelled cargo agents. As used herein, the term "affinity ligand" and "affinity tag" are used interchangeably and refer to a member of a specific binding pair, i.e. two molecules where one of the molecules through chemical or physical means specifically binds to the other molecule. In some cases, the complementary member of the affinity ligand may be immobilized (e.g., to a chromatography support, a bead or a planar surface) to produce an affinity chromatography support that specifically binds the affinity ligand. Tagging a compound of interest with an affinity ligand allows the compound to be separated from a mixture of untagged compounds by affinity, e.g., using affinity chromatography. Affinity ligands of interest include, but are not limited to, a biotin moiety. As used herein, the term "biotin moiety" refers to an affinity ligand that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$M. A biotin moiety may also include a linker, e.g., -LC-biotin, -LC-LC-Biotin, -SLC-Biotin or -PEG$_n$-Biotin where n is 3-12 (commercially available from Pierce Biotechnology).

Numerous detectable labels are of interest including, but not limited to, radioisotopes (radionuclides), metal-chelate complexes, fluorescent labels and enzyme-substrate labels.

Fluorescent labels or fluorophores of interest, include but are not limited to, fluorescein, 5-carboxyfluorescein, 6-carboxy fluorescein, 6-FAM, rhodamine, Texas Red, tetramethylrhodamine, carboxyrhodamine, carboxyrhodamine 6G, carboxyrhodol, carboxyrhodamine 110, Cascade Blue, Cascade Yellow, coumarin, Cy2, Cy3, Cy3.5, Cy5, Cy5.5, Cy-Chrome, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and-6)-carboxy-X-rhodamine), HEX, Lucifer Yellow, Marina Blue, Oregon Green 488, Oregon Green 500, Oregon Green 514, Alexa Fluor 350, Alexa Fluor 430, Alexa Fluor 488, Alexa Fluor 532, Alexa Fluor 546, Alexa Fluor 568, Alexa Fluor 594, Alexa Fluor 633, Alexa Fluor 647, Alexa Fluor 660, Alexa Fluor 680, 7-amino-4-methylcoumarin-3-acetic acid, BODIPY FL, BODIPY FL-Br.sub.2, BODIPY 530/550, BODIPY 558/568, BODIPY 564/570, BODIPY 576/589, BODIPY 581/591, BODIPY 630/650, BODIPY 650/665, BODIPY R6G, BODIPY TMR, BODIPY TR, TAMRA, dansyl, Lissamine; cyanines, phycoerythrins, Texas Red, analogs thereof, conjugates thereof, and combinations thereof. Exemplary lanthanide chelates include europium chelates, terbium chelates and samarium chelates. Fluorescent dyes and fluorescent label reagents include those which are commercially available from Invitrogen/Molecular Probes (Eugene, Oreg.) and Pierce Biotechnology, Inc. (Rockford, Ill.).

Carrier Proteins

Any convenient carrier proteins that include a thiol group or derivative thereof may be modified according to the subject methods. As used herein, the term "carrier protein" refers to a protein to which a cargo agent can be conjugated using the subject methods and which imparts upon the cargo agent a desirable biological activity or function. In some cases, the carrier protein is an endogenous protein which has a known biological activity or function. In some cases, the carrier protein has a desirable biological activity such as a long in vivo half-life. In certain cases, the carrier protein specifically binds a target protein. In certain instances, the carrier protein is localized in vivo to a desirable target location. In some embodiments, the carrier protein facilitates the diffusion and/or transport of a cargo agent across a biological membrane. In certain embodiments, the carrier protein is a serum protein of interest (e.g., a predominant serum protein present at a high concentration). A variety of carrier proteins are routinely used for use in different systems for presenting antigens and/or epitopes for eliciting an immune response, or for extending the in vivo half-life of an agent of interest.

In some cases, the carrier protein has a cysteine residue (e.g., a free cysteine residue in its thiol form, RSH). Since free thiol (RSH, sulfhydryl) groups are relatively reactive, proteins with cysteine residues can exist in their oxidized form as disulfide-linked oligomers or have internally bridged disulfide groups. In some embodiments of the subject methods, the method includes reducing a disulfide linkage of the carrier protein to produce free thiol groups suitable for chemoselective modification according to the subject methods. In some cases, the carrier protein may be engineered to include a cysteine residue. Engineering in cysteine thiol groups by the mutation of various amino acid residues of a protein to cysteine amino acids may be performed using any convenient methods. The engineered cysteine residue may be an unpaired (free Cys) residue or one which is relatively accessible for reaction. A "free cysteine" refers to a cysteine amino acid residue which has a thiol functional group (—SH), and is not paired as an intramolecular or intermolecular disulfide bridge.

In some cases, the carrier protein does not naturally include a cysteine residue, but may be chemically modified to include a thiol group (or derivative thereof) using any convenient method. Any convenient methods and reagents may be utilized to convert an amino acid residue of a carrier protein of interest (e.g., via the sidechain of the residue) into a thiol group (e.g., a thiolated residue). In certain cases, the thiolated amino acid residue is a Traut's reagent-derivatized lysine residue, i.e., a lysine residue that has been converted into a thiol containing residue via derivatization with Traut's reagent. The residue of interest that is derivatized may also be further protected, deprotected, and/or further conjugated to a linker of interest. For example, the conversion of lysine ε-amines into thiols can be accomplished with any convenient chemical agents, including but not limited to, N-succinimidyl S-acetylthioacetate (SATA), N-succinimidyl S-acetylthiopropionate (SATP), N-succinimidyl 3-2-pyridyldithio-propionate (SPDP), and 2-iminithiolane (2-IT, aka Tract's reagent).

Carrier proteins of interest include, but are not limited to, a serum transport protein such as albumin, alpha-fetoprotein, vitamin D-biding protein or afamin; keyhole limpet hemocyanin (KLH), ovalbumin (OVA), thyroglobulin (THY) and human gamma globulin (HGG). Albumin is the most abundant protein in human blood, at a concentration of approximately 600 μM. As used herein, "albumin" refers to the family of globular proteins that includes serum albumins, such as human serum albumin (HSA), bovine serum albumin (BSA) and rabbit serum albumin (RSA). In some cases, the carrier protein is albumin. In some cases, the carrier protein is human serum albumin. In some cases, the attachment site for a strained alkyne moiety is Cys-34 of human serum albumin (e.g., Cys-34 of mature HSA, i.e., HSA without the leader peptide. See, e.g. Minghetti et al. (1996) *J. Biol. Chem.* 261:6747; e.g., where Cys-34 is the Cys residue in the sequence Tyr-Leu-Gln-Gln-Cys-Pro-Phe-Glu-Asp-His-Val (SEQ ID NO:1), amino acids 30-40 of mature HSA.

Adducts

Aspects of the present disclosure include the conjugation of a strained alkyne-labelled cargo agent with a carrier protein to produce a carrier protein adduct.

In some cases, the in vivo half-life of a cargo agent present in a carrier-protein adduct of the present disclosure is at least 10%, at least 20%, at least 25%, at least 30%, at least 40%, at least 50%, at least 60%, at least 70%, at least 80%, at least 90%, at least 2-fold, at least 2.5-fold, at least 3-fold, at least 4-fold, at least 5-fold, at least 10-fold, at least 25-fold, at least 50-fold, at least 100-fold, or more than 100-fold (e.g., more than 200-fold, more than 500-fold, more than 1000-fold), higher than the in vivo half-life of the cargo agent in an unconjugated state (e.g., not conjugated to a carrier protein). The in vivo half-life can refer to the half-life of the unconjugated cargo agent or the adduct in circulation, e.g., in the blood.

In some embodiments, the adduct is described by Formula (II):

(II)

wherein A is cyclic group that is derived from the conjugation of a strained alkyne and a thiol of a carrier protein; P is a thiol-containing protein; $L^2$ is an optional linker; and Y is cargo agent (e.g., as described herein).

In some instances of Formula (II), Y is a therapeutic agent, a diagnostic agent, an antigen or an adjuvant. In certain instances of Formula (II), Y is a therapeutic agent. In certain instances of Formula (II), Y is a diagnostic agent. In certain instances of Formula (II), Y is an antigen or an adjuvant.

In some instances of Formula (II), A is a seven-membered ring. In some instances of Formula (II), A is an eight-membered ring. In some instances of Formula (II), A is a nine-membered ring. In some cases, the strained alkyne from which A is derived is a cyclooctyne.

In some instances of Formula (II), P is a cysteine-containing carrier protein. In some instances of Formula (II), P is a carrier protein that has been modified to include a thiol group.

Methods

Aspects of the present disclosure include a method of chemoselectively modifying a carrier protein, including: conjugating a carrier protein with a cyclooctyne-labeled cargo agent (e.g., as described herein) to produce a vinyl thioether-linked conjugate (e.g., as described herein). In some cases, the conjugating is performed in vitro, e.g., by contacting a sample including a carrier protein of interest with a strained alkyne-labelled cargo agent. In certain cases, the conjugating is performed in vivo and occurs spontaneously upon administration to a subject of a subject composition including a strained alkyne-labelled cargo agent. In such cases, the strained alkyne-labelled cargo agent may be conjugated to any convenient serum protein of interest, such as an albumin.

Aspects of the present disclosure include a method of increasing the in-vivo half-life of a bioactive agent. In some instances, the method includes: administering to a subject a pharmaceutical composition comprising a strained alkyne-labeled bioactive agent described by formula (III):

$$Z^1\text{-}L^1\text{-}W \qquad \text{(III)}$$

wherein $Z^1$ is a strained alkyne; $L^1$ is an optional linker; and W is a bioactive agent; to produce a vinyl thioether-linked conjugate. In some embodiments of formula (III), $Z^1$ is a cyclooctyne. The vinyl thioether-linked conjugate may be an adduct of the bioactive agent and an endogenous carrier protein. In some embodiments, the bioactive agent is a therapeutic agent. In some embodiments, the bioactive agent is a diagnostic agent. In some embodiments, the bioactive agent is a vaccine antigen. In certain embodiments, the carrier protein is an albumin.

Conjugation of a cargo agent (e.g., a bioactive agent) of interest to a carrier protein using the subject methods can be used to modify one or more biological properties of the cargo agent in vivo, relative to a cargo agent that has not been conjugated to the carrier protein. In some embodiments, the subject methods can provide a carrier protein adduct having lower clearance rates than that of the unbound cargo agent control. In some cases, by lower clearance rate is meant a clearance rate that is 50% or lower than the clearance rate of unbound cargo agent control, such as 40% or lower, 30% or lower, 20% or lower, 10% or lower, 5% or lower, or even 1% or lower than the clearance rate of unbound cargo agent.

The subject methods may provide a carrier protein adduct that exhibits prolonged lifetime profiles in vivo. In some embodiments, the carrier protein adduct has an extended half-life in vivo relative to unbound cargo agent control. In certain embodiments, the carrier protein adduct has a half-life ($t_{1/2}$) which is enhanced relative to the half-life of an unbound cargo agent control. For embodiments in which the half-life is enhanced, the half-life of the cargo agent of the carrier protein adduct is enhanced by at least 10%, such as at least 20%, at least 30%, at least 40%, at least 50%, at least 60%, at least 70%, at least 80%, at least 90%, at least 100%, at least 125%, at least 150%, at least 175%, at least 200%, at least 250%, at least 300%, at least 400% or at least 500%, or even by at least 1000% relative to the half-life of the unbound cargo agent control. In some embodiments, the half-life is determined in vitro, such as in a buffered saline solution or in serum. In other embodiments, the half-life is an in vivo half-life, such as the half-life of the cargo agent (e.g., a therapeutic agent) in the serum or other bodily fluid of an animal. In certain embodiments, the carrier protein adduct retains at least 50%, such as 60%, 70%, 80%, 85%, 90%, 95% or 100% of the biological activity associated with a cargo agent control.

Pharmaceutical Compositions

Also provided are pharmaceutical preparations that include a strained alkyne-labeled cargo agent (e.g., as described herein). In some embodiments of the pharmaceutical composition, the strained alkyne-labeled cargo agent is a strained alkyne-labeled therapeutic agent described by formula (IV):

$$Z^1\text{-}L^1\text{-}D \qquad \text{(IV)}$$

wherein $Z^1$ is a strained alkyne (e.g., as described herein); $L^1$ is an optional linker (e.g., as described herein); and D is a therapeutic agent (e.g., as described herein). In some cases, D is a vaccine antigen. In some cases, D is a chemotherapeutic agent. In some embodiments of formula (IV), $Z^1$ is a cyclooctyne.

Pharmaceutical preparations are compositions that include a compound (e.g., a strained alkyne-labeled therapeutic agent) (either alone or in the presence of one or more additional active agents) present in a pharmaceutically acceptable vehicle. The term "pharmaceutically acceptable" means approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a mammal, the compositions of the invention and pharmaceutically acceptable vehicles, excipients, or diluents may be sterile. In some instances, an aqueous medium is employed as a vehicle when the compound of the invention is administered intravenously, such as water, saline solutions, and aqueous dextrose and glycerol solutions.

Pharmaceutical compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In some instances, the pharmaceutical compositions are formulated for administration in accordance with routine procedures as a pharmaceutical composition adapted for oral or intravenous administration to humans. The choice of excipient will be determined in part by the particular compound, as well as by the particular method used to administer the composition. Accordingly, there is a wide variety of suitable formulations of the pharmaceutical composition of the present invention.

Administration of subject compositions may be systemic or local. In certain embodiments administration to a mammal will result in systemic release of a strained alkyne-labeled therapeutic agent (for example, into the bloodstream). Methods of administration may include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. In certain embodiments, the subject compositions are administered orally.

The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

The subject formulations can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

In some embodiments, formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are appropriate. In some embodiments the topical formulation contains one or more components selected from a structuring agent, a thickener or gelling agent, and an emollient or lubricant. Frequently employed structuring agents include long chain alcohols, such as stearyl alcohol, and glyceryl ethers or esters and oligo(ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components, e.g., astringents, fragrances, pigments, skin penetration enhancing agents, sunscreens (e.g., sunblocking agents), etc.

The subject compositions may also be formulated for oral administration. For an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition may also contain minor amounts of non-toxic auxiliary substances such as wetting agents, emulsifying agents, or buffers Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Dose levels can vary as a function of the specific compound, the nature of the delivery vehicle, and the like. Desired dosages for a given compound are readily determinable by a variety of means.

The dose administered to an animal, particularly a human, in the context of the present disclosure should be sufficient to effect a prophylactic or therapeutic response in the animal over a reasonable time frame, e.g., as described in greater detail below. Dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound.

In pharmaceutical dosage forms, the compounds may be administered in the form of a free base, their pharmaceutically acceptable salts, or they may also be used alone or in appropriate association, as well as in combination, with other pharmaceutically active compounds.

Utility

The methods and compositions of the present disclosure, e.g., as described above, find use in a variety of applications. Applications of interest include, but are not limited to: therapeutic applications, research applications, and diagnostic applications.

The subject methods and compositions find use in a variety of therapeutic applications. Therapeutic applications of interest include those applications in which the half-life of a therapeutic agent of interest is a factor in the treatment of a disease. As such, the subject methods and compositions find use in the treatment of a variety of different conditions in which the modulation (e.g., extension) of half-life of a therapeutic agent in the host is desired. Disease conditions of interest include, but are not limited to, cancer, hypertension, arrhythmia, and the like. Of interest in some cases is inhibition of angiogenesis.

The subject methods and compositions find use in a variety of diagnostic applications. Conjugates and adducts thereof that include a diagnostic agent such as a detectable label may be useful in biomedical imaging applications for localizing, visualizing, and quantitating a protein of interest, and binding or recognition events involving the same.

The subject methods and compositions find use in a variety of research applications. The subject compositions may be used to analyze the roles of target proteins in modulating various biological processes, including but not limited to, angiogenesis, inflammation, cellular growth, metabolism, regulation of transcription and regulation of phosphorylation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Figure 2:
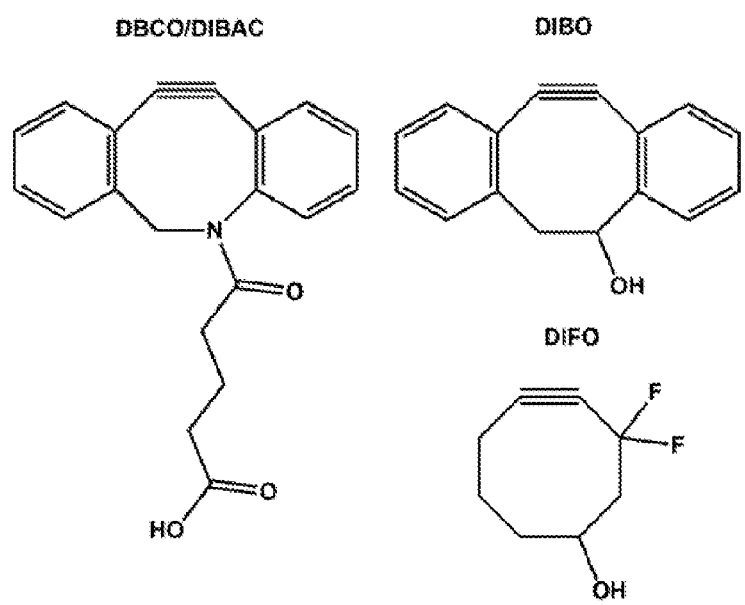
FIG. 2 depicts strained alkynes of interest that find use in the subject methods and compositions.

The thiol-yne reaction involves the addition of a thiol to an alkyne, to form a stable vinyl thioether. Linear alkynes may spontaneously react with biological thiols such as cysteines and glutathione; however, these reactions are slow, often requiring a proximity effect to achieve useful levels of modification. Alkynes also undergo pericyclic reactions with 1,3 dipoles. This fact has been exploited in the chemistry of cyclooctynes, the smallest cyclic alkynes (FIG. 2). Cyclooctynes are popular components of copper-free click chemistry due to their pericylic reactivity with azides and other pi systems. This strain-induced reactivity with azides concurrently accelerates their reactivity towards thiols and can lead to off-target reactivity with mouse serum albumin and other proteins, limiting their application in vivo.

FIG. 1. Cyclooctynes bind to serum albumin, positioning the alkyne in a favorable position to ligate to Cys 34 in a stable vinyl thioether linkage. Cargo attached to the cyclooctyne will have a longer serum half-life due to their conjugation to albumin.

FIG. 2. Cyclooctynes used in this study. DBCO/DIBAC=Dibenzoazocyclooctyne. DIBO=Dibenzocyclooctyne. DIFO=Difluorocyclooctyne This accelerated thiol-yne reactivity was exploited to generate the novel albumin conjugation reaction (FIG. 1) of the present disclosure. To establish proof-of-principle, human or mouse serum was incubated with a panel of cyclooctyne-fluorophore conjugates for 2 h at 37° C., the proteins were resolved by reducing and denaturing PAGE to disrupt any non-covalent interactions, and then the gel was scanned for fluorescence signal. The labeling of a protein around 70 kDa was detected, consistent with the molecular mass of serum albumin. This labeling pattern was observed for three cyclooctynes in both mouse and human serum (FIG. 3, DIBAC not shown).

Figure 3:
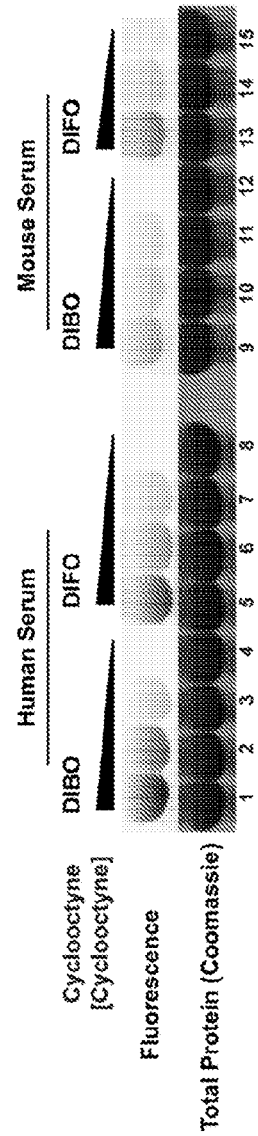
FIG. 3 shows polyacrylamide gel images which illustrate that cyclooctyne-fluorophore conjugates of interest react selectively with human or mouse serum.

FIG. 3. Cyclooctynes react selectively with serum albumin. Cyclooctyne-fluorophore conjugates were incubated with human or mouse serum for 2 h at 37° C. High concentration was 100 µM, medium concentration was 25 µM, and low concentration was 6.25 µM. The fourth lane in each series is a no cyclooctyne negative control. Labeled serum was then diluted 1:10 in phosphate-buffered saline (PBS), resolved by polyacrylamide gel electrophoresis (PAGE), and scanned for fluorescence. The gel was then incubated in Coomassie and imaged to determine total protein content. DIBO=Dibenzylcyclooctyne. DIFO=Difluorocyclooctyne.

In a further experiment was provided human serum that was pre-labeled with cyclooctyne-fluorophore conjugates and selectively depleted serum albumin with Cibacron Blue resin, and then bound proteins were eluted from the resin with 1.5 M NaCl. All samples were analyzed by PAGE and fluorescence scanning. Upon albumin depletion, the fluorescent band on the gel was reduced in size and intensity. Elution from the resin recovered a protein of similar weight to the originally labeled band (FIG. 4).

Figure 4:
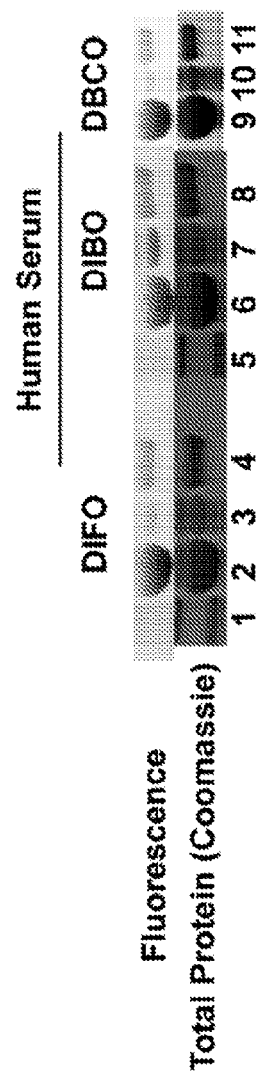
FIG. 4 shows polyacrylamide gel images that illustrate the cyclooctyne-fluorophore conjugate labeled band of albumin from serum (FIG. 3) is selectively depleted with albumin-binding resin.

FIG. 4. Labeled band is selectively depleted with albumin-binding resin. Serum was labeled with 20 µM cyclooctyne-fluorophore conjugate as in FIG. 4. Lanes 2, 6, and 9 were left untreated while 3, 7, and 10 were treated with Cibacron Blue resin to deplete albumin. Bound albumin was eluted from the column with 1.5 M NaCl and loaded in lanes 4, 8, and 11. Lanes 1 and 5 are protein ladder.

Next, serum was incubated with biotin conjugates of the cyclooctynes to confirm that this interaction was not an artifact of a potential interaction of albumin with the fluorophores and truly a covalent interaction (FIG. 5). The biotinylated serum proteins were then enriched by pulldown with streptavidin beads and washed extensively in 1% sodium dodecyl sulfate-PBS (SDS-PBS), 3M urea, 1M NaCl, and then PBS. Remaining proteins were eluted by boiling in 4X SDS loading buffer at 90° C. for 15 min. The supernatant was loaded onto a reducing and denaturing PAGE and total protein was detected by Coomassie. For serum samples containing the biotinylated cyclooctyne, a sharp band corresponding to serum albumin was present. This band was absent in samples missing the cyclooctyne.

FIG. 5. Streptavidin enrichment of biotinylated albumin. Human or mouse serum was treated with 20 µM biotin-cyclooctyne conjugate or PBS for 2 h at 37° C. The samples were diluted and incubated with streptavidin-agarose resin for 1 h at room temperature (RT). The resin was washed in SDS-PBS, 3M Urea, 1M NaCl, and PBS and then boiled in 4× loading buffer for 15 min. The supernatant was then resolved by PAGE and then imaged by Coomassie total protein stain.

An aptamer-cyclooctyne conjugate was made to test the efficiency of albumin labeling. Aptamers are single stranded nucleic acids that have been selected to bind unique targets, analogous to antibodies. Several aptamer based therapeutics are on the market, such as Macugen for macular degeneration. Due to their small size, aptamers are notoriously short lived in serum, and often rely on PEGylation to increase their hydrodynamic radius and reduce clearance. Conjugation to albumin represents a new way to increase the half-life of aptamer therapeutics. The aptamer-cyclooctyne conjugate was incubated with human serum or recombinant human albumin for 2 h at 37° C. and then the proteins were separated using PAGE. The aptamer also possessed a fluorophore to enable easy detection. Upon fluorescence analysis, a mass shift was observed in both lanes, suggesting covalent modification of albumin with the aptamer conjugate (FIG. 6).

FIG. 6. Aptamer-cyclooctyne conjugates label albumin in whole serum. Cyclooctyne-fluorophore conjugates (fluorophore-cyclooctyne-aptamer conjugate in Lanes 1-3, cyclooctyne-fluorophore conjugate in Lanes 4-6) were incubated with whole human serum (Lanes 1 and 4), purified human albumin (Lanes 2 and 5), or PBS (Lanes 3 and 6) for 2 h at 37° C. All samples were resolved by PAGE and scanned for fluorescence.

Taken together, these experiments establish that strained alkynes can be used to selectively modify albumin with moieties such as small molecules and nucleic acids. The strained alkyne-labelled cargo agents and methods described herein represent an advance over other methods of albumin conjugation due to superior hydrolytic stability, solubility, ease of synthesis, and selectivity of modification.

Notwithstanding the appended claims, the disclosure set forth herein is also described by the following clauses.

1. A pharmaceutical composition, comprising a strained alkyne-labeled therapeutic agent described by formula (I): $Z^1$-$L^1$-D (I), wherein $Z^1$ is a strained alkyne; $L^1$ is an optional linker; and D is a therapeutic agent.

2. The pharmaceutical composition of Clause 1, wherein $Z^1$ is a cyclooctyne.

3. The pharmaceutical composition of Clause 1, wherein the strained alkyne-labeled therapeutic agent exhibits a serum half-life at least 10% greater than the serum half-life of an unlabeled therapeutic agent.

4. The pharmaceutical composition of any one of Clauses 1-3, wherein $L^1$ is a cleavable linker.

5. The pharmaceutical composition of any one of Clauses 1-4, wherein the strained alkyne is selected from: dibenzoazocyclooctyne, a dibenzocyclooctyne, a difluorocyclooctyne, OCT1, OCT2, OCT3, MOFO, BCN, TMTH, DIMAC, BARAC and COMBO.

6. The pharmaceutical composition of any one of Clauses 1-5, wherein the therapeutic agent is a chemotherapeutic agent.

7. A strained alkyne-carrier protein adduct, described by Formula (II):

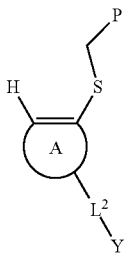

(II)

wherein A is group comprising a ring that is derived from the conjugation of a strained alkyne and a thiol group of a carrier protein; P is a thiol containing carrier protein; L² is an optional linker; and Y is a therapeutic agent, a diagnostic agent, an antigen or an adjuvant.

8. The adduct of Clause 7, wherein A is group comprising an eight-membered ring that is derived from the conjugation of a cyclooctyne and a cysteine residue of a cysteine-containing carrier protein; and P is a cysteine containing carrier protein.

9. The adduct of any one of Clauses 7-8, wherein Y is a therapeutic agent selected from the group consisting of a small molecule, a polynucleotide, a lipid, and a polypeptide.

10. The adduct of any one of Clauses 7-9, wherein Y is selected from growth hormone, GLP1, GLP2, folate, exendin4 and doxorubicin.

11. The adduct of any one of Clauses 7-9, wherein Y is a diagnostic agent.

12. The adduct of any one of Clauses 7-11, wherein P is human serum albumin.

13. The adduct of any one of Clauses 7-12, wherein L¹ is a cleavable linker.

14. The adduct of Clause 8, wherein the cyclooctyne is selected from: dibenzoazocyclooctyne, a dibenzocyclooctyne, a difluorocyclooctyne, OCT1, OCT2, OCT3, MOFO, BCN, TMTH, DIMAC, BARAC and COMBO.

15. The adduct of any one of Clauses 7-14, wherein the adduct exhibits a serum half-life at least 10% greater than the serum half-life of an unlabeled therapeutic agent.

16. A method of chemoselectively modifying a carrier protein, comprising: conjugating a thiol group of a carrier protein with a strained alkyne-labeled cargo agent to produce a vinyl thioether-linked conjugate.

17. The method of Clause 16, wherein the carrier protein is a cysteine-containing carrier protein and the strained alkyne-labeled cargo agent is a cyclooctyne-labeled cargo agent.

18. The method of Clause 16, wherein the vinyl thioether-linked conjugate is described by Formula (II):

(II)

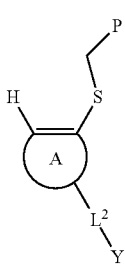

wherein A is a group comprising a ring that is derived from the conjugation of the strained alkyne and the thiol group; P is the carrier protein; L² is an optional linker; and Y is the cargo agent.

19. The method of Clause 16, wherein the conjugating is performed in vitro.

20. The method of Clause 16, wherein the conjugating is performed in vivo.

21. A method of increasing the in vivo half-life of a bioactive agent, the method comprising: administering to a subject a pharmaceutical composition comprising a strained alkyne-labeled bioactive agent described by formula (III):

$$Z^1\text{-}L^1\text{-}W \qquad \text{(III)}$$

wherein Z¹ is a strained alkyne; L¹ is an optional linker; and W is a bioactive agent; to produce a vinyl thioether-linked conjugate.

22. The method of clause 21, wherein the strained alkyne is a cyclooctyne.

23. The method of clause 21, wherein the in vivo half-life of the bioactive agent is increased by at least 10% (e.g., at least 20%, at least 30%, etc) relative to unlabeled bioactive agent.

24. The method of clause 21, wherein the administering treats a disease or disorder.

25. The method of clause 24, wherein the disease or disorder is cancer, an inflammatory disease or an infectious disease.

26. The method of any one of clauses 21-25, wherein the subject is a primate.

27. The method of clause 26, wherein the primate is a human.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A pharmaceutical composition, comprising a strained alkyne-labeled therapeutic agent described by Formula (I):

$$Z^1\text{-}L^1\text{-}D \qquad \text{(I)}$$

wherein:

Z¹ is a cyclooctyne selected from a dibenzoazocyclooctyne (DBCO/DIBAC), a dibenzocyclooctyne (DIBO), a difluorocyclooctyne (DIFO), OCT1, OCT2, OCT3, MOFO, BCN, TMTH, DIMAC, BARAC and COMBO;

L¹ is an optional linker; and

D is a polynucleotide.

2. The pharmaceutical composition of claim 1, wherein Z¹ is:

4. The pharmaceutical composition of claim 1, wherein $Z^1$ is:

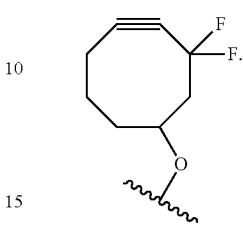

3. The pharmaceutical composition of claim 1, wherein $Z^1$ is:

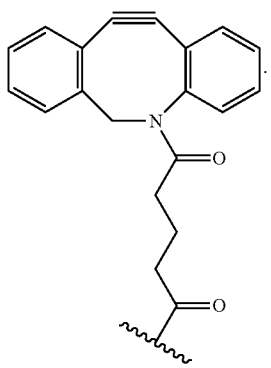 [SMILES: *C(=O)CCCC(=O)N1Cc2ccccc2C#Cc2ccccc21]

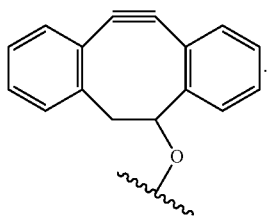 [SMILES: *OC1Cc2ccccc2C#Cc2ccccc21]

5. The pharmaceutical composition of claim 1, wherein $L^1$ is selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl.

6. The pharmaceutical composition of claim 1, further comprising a fluorophore.

\* \* \* \* \*

UNITED STATES PATENT AND TRADEMARK OFFICE
CERTIFICATE OF CORRECTION

PATENT NO. : 11,135,299 B2  
APPLICATION NO. : 15/576226  
DATED : October 5, 2021  
INVENTOR(S) : Peter V. Robinson et al.

It is certified that error appears in the above-identified patent and that said Letters Patent is hereby corrected as shown below:

On the Title Page

Item [73], should read as The Regents of the University of California, Oakland, CA (US); and In the Specification In Column 15, Line 13, replace "opthalmological" with --- ophthalmological ---.

Signed and Sealed this  
Twenty-ninth Day of March, 2022

Drew Hirshfeld  
*Performing the Functions and Duties of the  
Under Secretary of Commerce for Intellectual Property and  
Director of the United States Patent and Trademark Office*